United States Patent [19]

Prasad et al.

[11] Patent Number: 5,895,818
[45] Date of Patent: Apr. 20, 1999

[54] PROCESS FOR MAKING N-(4-FLUOROPHENYL)-N-(1-METHYLETHYL)-2-|(5-TRIFULOROMETHYL)-1,3,4-THIADIAZOL-2-YL)OXY|ACETAMIDE USING AN APROTIC, AROMATIC SOLVENT

[75] Inventors: Vidyanatha A. Prasad; Peter E. Newallis, both of Leawood, Kans.; Daniel M. Wasleski, Raytown; Jacqueline M. Applegate, Parkville, both of Mo.; Klaus Jelich, Overland Park, Kans.

[73] Assignee: Bayer Corporation, Pittsburgh, Pa.

[21] Appl. No.: 08/989,597

[22] Filed: Dec. 12, 1997

[51] Int. Cl.$^6$ .................................................. C07D 285/13
[52] U.S. Cl. ............................................................ 548/136
[58] Field of Search ............................................... 548/136

[56] References Cited

U.S. PATENT DOCUMENTS

| | | |
|---|---|---|
| 4,585,471 | 4/1986 | Förster et al. ........................ 71/90 |
| 4,645,525 | 2/1987 | Förster et al. ........................ 71/88 |
| 4,756,741 | 7/1988 | Förster et al. ........................ 71/90 |
| 4,968,342 | 11/1990 | Förster et al. ........................ 71/90 |
| 5,090,991 | 2/1992 | Förster et al. ........................ 71/90 |
| 5,101,034 | 3/1992 | Schmidt et al. ...................... 548/136 |

*Primary Examiner*—Robert Gerstl
*Attorney, Agent, or Firm*—Joseph C. Gil; Carol Marmo

[57] ABSTRACT

The present invention relates to a process for making N-(4-fluorophenyl)-N-(1-methylethyl)-2-|(5-trifluoromethyl)-1,3,4-thiadiazol-2-yl)oxy|acetamide in an aprotic, aromatic solvent. The process includes the steps of: (a) reacting 2-(methylsulfonyl)-5-(trifluoromethyl)-1,3,4-thiadiazole with N-(4-fluorophenyl)-2-hydroxy-N-(1-methylethyl)acetamide in the presence of an aprotic, aromatic solvent to form an aqueous phase and an organic phase; (b) acidifying the phases, (c) separating the phases; and (d) recovering the N-(4-fluorophenyl)-N-(1-methylethyl)-2-|(5-trifluoromethyl)-1,3,4-thiadiazol-2-yl)oxy|acetamide from the organic phase.

22 Claims, No Drawings

PROCESS FOR MAKING N-(4-FLUOROPHENYL)-N-(1-METHYLETHYL)-2-|(5-TRIFULOROMETHYL)-1,3,4-THIADIAZOL-2-YL)OXY|ACETAMIDE USING AN APROTIC, AROMATIC SOLVENT

TECHNICAL FIELD OF THE INVENTION

The field of this invention is the synthesis of acetamide herbicides. More particularly, this invention relates to processes for making, recovering and isolating N-(4-fluorophenyl)-N-(1-methylethyl)-2-|(5-trifluoromethyl)-1,3,4-thiadiazol-2-yl)oxy|acetamide.

BACKGROUND OF THE INVENTION

Certain azolyloxy-carboxylic acid amides and heteroaryloxy-acetamides of the general formula R—O—CH($R^1$)—CO—N($R^2$)($R^3$) are known to have herbicidal activity (See, e.g., U.S. Pat. Nos. 4,756,741 and 5,101,034). U.S. Pat. No. 5,101,034 discloses a particular class of heteroaryloxyacetamides, namely thiadiazole acetamides as having herbicidal activity. The thiadiazole acetamides are made by reacting a thiadiazole sulfone with an hydroxyacetanilide in acetone. Of particular relevance to the present invention is the disclosure of a synthetic scheme for making 2-(5-trifluoromethyl)-1,3,4-thiadiazol-2-yl-oxy)-N-methylacetanilide. In accordance with that synthetic scheme, 2-methylsulfonyl-5-trifluoromethyl-1,3,4-thiadiazole is reacted with N-methyl-2-hydroxyacetanilide, potassium carbonate, and tetraethylammonium bromide. Acetone is used as the solvent for the reaction. The reaction is carried out at a temperature of 20° C.–25° C. for 20 hours. Undissolved salts are filtered off and washed with acetone. The filtrate is freed of solvent in vacuo and the resulting residue taken up in diethyl ether, washed with dilute hydrochloric acid, dried and filtered. After freeing the filtrate of solvent, the end product is crystallized from the oily residue. Reported yields are about 90%.

U.S. Pat. Nos. 4,756,741 and 4,645,525 disclose a synthetic scheme for making O-(2-trifluoromethyl-1,3,4,-thiadiazol-5-yl-oxo)acetic N-methylanilide. In accordance with that scheme, 2-hydroxy-acetic acid-N-methylanilide is reacted with dimethylsulfoxide and calcium oxide at 50° C. for 1 hour. 5-Bromo-2-trifluoromethyl-1,3,4-thidiazole is then added to the reaction mixture and the mixture stirred at 50° C. for 40 hours. The mixture is then poured into water and the oil that precipitates is extracted with methylene chloride. The end product is obtained in about 90% yield by distilling off the methylene chloride.

U.S. Pat. No. 4,585,471 discloses synthetic schemes for making (5-trifluoromethyl-1,3,4-thiadiazol-2-yl-oxy)-acetic acid 2-ethylpiperidine and (5-trifluoromethyl-1,3,4-thiadiazol-2-yl-oxy)-acetic acid 2-methylpiperidine. In accordance with those synthetic schemes, the ethylpiperidine compound is made by reacting hydroxyacetic acid-2-ethylpiperidine with 2-chloro-5-trifluoromethyl-1,3,4-thiadiazole in the presence of potassium tert-butanate in tert-butanol at a temperature of 20° C. to 30° C. for 3 hours and the methylpiperidine compound is made by reacting 2-chloro-5-trifluoromethyl-1,3,4-thiadiazole in toluene with hydroxyacetic acid-2-methylpiperidine in the presence of sodium hydroxide. The end product, in both cases, is recovered from the reaction mixture by acidification with hydrochloric acid, drying, removal of solvent and crystallization. The reported yields of the end-products were 66% (ethylpiperidine) and 54% (methylpiperidine).

U.S. Pat. Nos. 4,968,342 and 5,090,991 disclose a synthetic scheme for making N-isopropyl-(5-trifluoromethyl-1,3,4,-thiadiazol-2-yl)-3'-chlorooxyacetanilide. In accordance with that scheme, 2-methylsulfonyl-5-trifluoromethyl-1,3,4-thiadiazole, dissolved in acetone, with 3'-chloro-N-isopropylhydroxyacetanilide in the presence of sodium hydroxide and water for 3 hours at –20° C. Water is added to the reaction mixture and the crystalline end-product obtained by crystallization in 85% yield.

It can be seen from the above, that existing methods for making acetamide herbicides suffer from low yields (54% to 85%), prolonged reaction times (20 to 40 hours) or the use of problematic solvents (acetone). There continues to be a need in the art, therefore, for a practical method for making these herbicides, which method avoids the problems of the existing art.

BRIEF SUMMARY OF THE INVENTION

The present invention provides a process for preparing N-(4-fluorophenyl)-N-(1-methylethyl)-2-|(5-trifluoromethyl)-1,3,4-thiadiazol-2-yl)oxy|acetamide. The process includes the steps of: (a) reacting 2-(methylsulfonyl)-5-(trifluoromethyl)-1,3,4-thiadiazole with N-(4-fluorophenyl)-2-hydroxy-N-(1-methylethyl) acetamide in the presence of an aprotic, aromatic solvent to form an aqueous phase and an organic phase; (b) separating the phases; and (c) recovering the N-(4-fluorophenyl)-N-(1-methylethyl)-2-[(5-trifluoromethyl)-1,3,4-thiadiazol-2-yl)oxy|acetamide from the organic phase. The solvent is preferably toluene, xylene, cumene or mesitylene and, more preferably toluene. In a preferred embodiment, reaction occurs in the presence of an aqueous alkali. The aqueous alkali is preferably an aqueous alkali metal carbonate or an aqueous alkali metal hydroxide where the alkali metal is sodium. Most preferably, the aqueous alkali is aqueous sodium hydroxide.

As a result of alkali use, the aqueous phase has a pH of from about 11 to about 14, more preferably a pH of about 13. The reaction of 2-(methylsulfonyl)-5-(trifluoromethyl)-1,3,4-thiadiazole with N-(4-fluorophenyl)-2-hydroxy-N-(1-methylethyl)acetamide in solvent is carried out at a temperature of from about 0° C. to about 30° C., preferably from about 5° C. to about 15° C. The molar ratio of 2-(methylsulfonyl)-5-(trifluoromethyl)-1,3,4-thiadiazole to N-(4-fluorophenyl)-2-hydroxy-N-(1-methylethyl)acetamide is from about 1.5:1 to about 1:1.5, preferably about 1:1. The molar ratio of solvent to 2-(methylsulfonyl)-5-(trifluoromethyl)-1,3,4-thiadiazole is from about 1:1 to about 5:1.

In one embodiment, a process of the present invention using alkali further includes the step of acidifying the aqueous phase before phase separation. The aqueous phase is acidified to a pH of from about 2.0 to about 6.0 and preferably to a pH of from about 3.0 to about 5.0. The reaction mixture is treated with hydrochloric acid or sulfuric acid. The reaction mixture can be heated to a temperature of from about 10° C. to about 80° C., filtered and the organic and aqueous phases are separated. The N-(4-fluorophenyl)-N-(1-methylethyl)-2-|(5-trifluoromethyl)-1,3,4-thiadiazol-2-yl)oxy|acetamide is recovered by acidifying the organic phase, removing the solvent from the organic phase via steam distillation or vacuum distillation to form a molten mother liquor mixture and isolating the N-(4-fluorophenyl)-N-(1-methylethyl)-2-|(5-trifluoromethyl)-1,3,4-thiadiazol-2-yl)oxy|acetamide from the molten residue.

In a preferred embodiment, a process for preparing N-(4-fluorophenyl)-N-(1-methylethyl)-2-|(5-trifluoromethyl)-1,3,4-thiadiazol-2-yl)oxy|acetamide includes the steps of adding 2-(methylsulfonyl)-5-(trifluoromethyl)-1,3,4-thiadiazole in toluene and N-(4-fluorophenyl)-2-hydroxy-N-(1-methylethyl)acetamide in toluene to a reaction vessel, cooling the reaction mixture to about 0° C.–5° C., adding an aqueous solution of sodium hydroxide and maintaining the reaction mixture at a temperature of from about 5° C. to about 15° C. for a period of time ranging from about 1 hour to about 3 hours to form an aqueous phase, an alkaline rag phase and an organic phase having a pH of from about 11 to about 14, acidifying the aqueous phases, heating the phases to a temperature of from about 10° C. to about 20° C., filtering the reaction mixture, separating the phases, and recovering the N-(4-fluorophenyl)-N-(1-methylethyl)-2-[(5-trifluoromethyl)-1,3,4-thiadiazol-2-yl)oxy]acetamide from the organic phase.

DETAILED DESCRIPTION OF THE INVENTION

I. The Invention

The present invention relates to processes for the synthesis, recovery and isolation of the herbicide, N-(4-fluorophenyl)-N-(1-methylethyl)-2-[(5-trifluoromethyl)-1,3,4-thiadiazol-2-yl)oxy]acetamide. The synthetic process includes the step of reacting 2-(methylsulfonyl)-5-(trifluoromethyl)-1,3,4-thiadiazole with N-(4-fluorophenyl)-2-hydroxy-N-(1-methylethyl)acetamide and aqueous NaOH in the presence of an aprotic, aromatic solvent. Formed N-(4-fluorophenyl)-N-(1-methylethyl)-2-[(5-trifluoromethyl)-1,3,4-thiadiazol-2-yl)oxy]acetamide can be recovered after acidification followed by phase separation and removal of solvent from the organic phase.

II. Method of Making N-(4-fluorophenyl)-N-(1-methylethyl)-2-[(5-trifluoromethyl)-1,3,4-thiadiazol-2-yl)oxy]acetamide Using an Aprotic, Aromatic Solvent The process for making N-(4-fluorophenyl)-N-(1-methylethyl)-2-[(5-trifluoromethyl)-1,3,4-thiadiazol-2-yl)oxy]acetamide includes the step of reacting 2-(methylsulfonyl)-5-(trifluoromethyl)-1,3,4-thiadiazole with N-(4-fluorophenyl)-2-hydroxy-N-(1-methylethyl)acetamide in an aprotic, aromatic solvent. The solvent is preferably toluene, xylene, cumene or mesitylene and, most preferably toluene.

The 2-(methylsulfonyl)-5-(trifluoromethyl)-1,3,4-thiadiazole (TDA sulfone) and the N-(4-fluorophenyl)-2-hydroxy-N-(1-methylethyl)acetamide (FOE hydroxy) used in the present process can be made using any method. Preferred means for making TDA sulfone can be found in United States Patent Applications entitled "Synthesis of Sulfoxides Using Controlled Oxidation of Sulfides with Perborate or Percarbonate", "Synthesis of 2-(Methylsulfonyl)-5-(Trifluoromethyl)-1,3,4-Thiadiazole Using Oxidation of 2-(Methylthio)-5-(Trifluoromethyl)-1,3,4-Thiadiazole with a Molybdenum or Tungsten Catalyst", and "Synthesis of 2-(Methylsulfonyl)-5-(Trifluoromethyl)-1,3,4-Thiadiazole Using Oxidation of 2-(Methylthio)-5-(Trifluoromethyl)-1,3,4-Thiadiazole with Acetic Acid", filed concurrently herewith. Preferred means for making FOE hydroxy can be found in United States Patent Applications entitled "Conversion of N-(4-Fluorophenyl)-2-Hydroxy-N-(1-Methylethyl) Acetamide Acetate to N(4-Fluorophenyl)-2-Hydroxy-N-(1-Methylethyl) Acetamide Using Aqueous Alkali," "Method of Making N-(4-Fluorophenyl)-2-Hydroxy-N-(1-Methylethyl Acetamide Using Sodium Formate," and "Conversion of N-(4-Fluorophenyl)-2-Hydroxy-N-(1-Methylethyl) Acetamide Acetate to N-(Fluorophenyl)-2-Hydroxy-N-(1-Methylethyl) Acetamide Using Water and Solvent," filed concurrently herewith. The disclosures of all five of these patent applications are incorporated herein by reference. The molar ratio of 2-(methylsulfonyl)-5-(trifluoromethyl)-1,3,4-thiadiazole to N-(4-fluorophenyl)-2-hydroxy-N-(1-methylethyl)acetamide is from about 1.5:1 to about 1:1.5 and more preferably about 1:1.

Where the TDA sulfone and FOE hydroxy are not provided in the solvent, the solvent is added to the reaction mixture. The molar ratio of solvent (e.g., toluene) to either TDA sulfone or FOE hydroxy is from about 1:1 to about 5:1. The solvent is preferably present in a molar excess relative to TDA sulfone and FOE hydroxy. The reaction preferably uses purified reactants. As set forth hereinafter in the Examples, the use of highly purified TDA sulfone and FOE hydroxy results in enhanced purity and yield of N-(4-fluorophenyl)-N-(1-methylethyl)-2-[(5-trifluoromethyl)-1,3,4-thiadiazol-2-yl)oxy]acetamide. The purity of the TDA sulfone is preferably greater than about 95% A.I., more preferably greater than about 97.5% A.I. and, even more preferably greater than about 99.0% A.I. The purity of the FOE hydroxy is preferably greater than about 94.0% A.I., more preferably greater than about 96.0% A.I., even more preferably greater than about 98.0% A.I and, most preferably greater than about 99.0% A.I.

The reaction of TDA sulfone and FOE hydroxy typically occurs at a relatively cool temperature. Preferably the reaction temperature is from about 0° C. to about 30° C. More preferably, the temperature is from about 0° C. to about 15° C. and, most preferably from about 0° C. to about 5° C.

In a preferred embodiment, the reaction occurs in the presence of an aqueous alkali. Exemplary and preferred aqueous alkalis are aqueous alkali metal hydroxides or carbonates. Alkali metal hydroxides and carbonates are well known in the art. Exemplary and preferred alkali metals are potassium, sodium and lithium. Sodium is most preferred. The molar ratio of the aqueous alkali (e.g., sodium hydroxide) to the primary reactants (e.g., TDA sulfone and FOE hydroxy) is from about 1:1 to about 2:1 and, preferably from about 1.25:1 to about 1.75:1. The aqueous alkali is added to the reaction mixture as an aqueous solution of the hydroxide or carbonate. Preferably the alkali metal hydroxide or carbonate concentration of the solution is from about 20 weight percent to about 60 weight percent. More preferably, the alkali concentration is from about 25 weight percent to about 50 weight percent.

The aqueous alkali can be added at a single time or added in portions over a prolonged period of time. The yield and purity of the formed N-(4-fluorophenyl)-N-(1-methylethyl)-2-[(5-trifluoromethyl)-1,3,4-thiadiazol-2-yl)oxy]acetamide is enhanced where the alkali is added slowly over a period of from about 1 hour to about 3 hours. The mixture of TDA sulfone and FOE hydroxy is agitated during the entire time over which the alkali is added.

In an especially preferred embodiment, the process includes the steps of adding 2-(methylsulfonyl)-5-(trifluoromethyl)-1,3,4-thiadiazole in toluene and N-(4-fluorophenyl)-2-hydroxy-N-(1-methylethyl)acetamide in toluene to a reaction vessel to form a reaction mixture, cooling the reaction mixture to about 0° C.–5° C., adding an aqueous solution of sodium hydroxide to the reaction mixture slowly over 1 to 3 hours and maintaining the reaction mixture at a temperature of from about 0° C. to about 5° C. for a period of time ranging from about 1 hour to about 3 hours.

A sufficient amount of alkali is used so as to raise the pH of the aqueous phase to a pH of from about 11 to about 14. Preferably, the pH is raised to a level of from about 12 to about 14. Means for determining the amount of a particular alkali needed to cause such an increase in pH are well known in the art.

The process can further include the step of recovering the N-(4-fluorophenyl)-N-(1-methylethyl)-2-|(5-trifluoromethyl)-1,3,4-thiadiazol-2-yl)oxy|acetamide. Recovery can be accomplished using any well known recovery method. Preferably, recovery is accomplished using acid as set forth below. A process of the present invention produces N-(4-fluorophenyl)-N-(1-methylethyl)-2-|(5-trifluoromethyl)-1,3,4-thiadiazol-2-yl)oxy|acetamide in yields of greater than about 90% (based on either TDA sulfone or FOE hydroxy) with a purity of over 90% A.I.

III. Recovery of N-(4-fluorophenyl)-N-(1-methylethyl)-2-|(5-trifluoromethyl)-1,3,4-thiadiazol-2-yl)oxy|acetamide via Acidification Before Phase Separation In an especially preferred embodiment, N-(4-fluorophenyl)-N-(1-methylethyl)-2-|(5-trifluoromethyl)-1,3,4-thiadiazol-2-yl)oxy|acetamide is made and recovered according a process that includes the steps of adding 2-(methylsulfonyl)-5-(trifluoromethyl)-1,3,4-thiadiazole in toluene and N-(4-fluorophenyl)-2-hydroxy-N-(1-methylethyl)acetamide in toluene to a reaction vessel to form a reaction mixture, cooling the reaction mixture to about 0° C.–5° C., adding an aqueous solution of sodium hydroxide to the reaction mixture and maintaining the reaction mixture at a temperature of from about 0° C. to about 15° C. for a period of time ranging from about 1 hour to about 3 hours to form a reaction product.

It may be desirable to convert the reaction mixture to an acid pH prior to isolation of the FOE. In accordance with this embodiment, the phases are treated with acid before phase separation. Preferably, the pH is lowered to a value of from about 2.0 to about 6.0 and, more preferably, to a value of from about 3.0 to about 5.0.

Acidification is accomplished by treating the reaction mixture with a suitable amount of mineral acid. Means for determining the amount of acid needed are well known in the art and will depend, inter alia, on the acid used. Suitable mineral acids include sulfuric acid, hydrochloric acid and nitric acid. Hydrochloric and sulphuric acid are most preferred. Following acidification, the phases are separated and the process continues as set forth above in Section III.

The organic phase containing the N-(4-fluorophenyl)-N-(1-methylethyl)-2-|(5-trifluoromethyl)-1,3,4-thiadiazol-2-yl)oxy|acetamide is acidified to a pH of from about 1.5 to about 4.5, more preferably to a pH of from about 1.5 to about 3.0 and, even more preferably to a pH of from about 1.5 to about 2.5. Means for determining the amount of acid needed to acidify the organic phase are well known in the art. Acidification is accomplished by adding a concentrated mineral acid to the organic phase. Suitable mineral acids are hydrochloric acid, nitric acid and sulfuric acid. Sulfuric acid is preferred. The concentration of sulfuric acid is preferably about 70 weight percent.

N-(4-fluorophenyl)-N-(1-methylethyl)-2-|(5-trifluoromethyl)-1,3,4-thiadiazol-2-yl)oxy|acetamide can be recovered from the acidified organic phase using any means well known in the art. Exemplary such recovery means include flaking, distillation, extraction and crystallization. A preferred means of recovery is flaking as described below. As set forth hereinafter in the Examples, recovery using acidification results in yields of greater than about 90%.

IV. Isolation of N-(4-fluorophenyl)-N-(1-methylethyl)-2-|(5-trifluoromethyl)-1,3,4-thiadiazol-2-yl)oxy|acetamide In another aspect, the present invention provides a process for isolating N-(4-fluorophenyl)-N-(1-methylethyl)-2-|(5-trifluoromethyl)-1,3,4-thiadiazol-2-yl)oxy|acetamide. In accordance with this process, N-(4-fluorophenyl)-N-(1-methylethyl)-2-|(5-trifluoromethyl)-1,3,4-thiadiazol-2-yl)oxy|acetamide, obtained by any means, is dissolved or suspended in an aprotic, aromatic solvent such as toluene and isolated from the toluene. Isolation is typically accomplished by removing the solvent from the solution of N-(4-fluorophenyl)-N-(1-methylethyl)-2-|5-trifluoro-methyl)-1,3,4-thiadiazol-2-yl)oxy|acetamide to form a solvent-free material. Melting the material, spreading the molten material out on a solid surface and allowing the product to crystallize.

Solvent can be removed from the solution using any means well known in the art. A preferred means of solvent removal is evaporation. Preferably, evaporation is preformed under a negative pressure using a vacuum apparatus. Evaporation typically occurs at a temperature of from about 60° C. to about 85° C. The molten materials is then spread out in a thin layer on a solid surface, cooled to a temperature of from about 20° C. to about 30° C. (room temperature) and maintained at that temperature until crystallization. The product crystallizes as aggregates of flakes on the cooled solid surface.

The Examples to follow illustrate preferred embodiments of the present invention and are not limiting of the claims and specification in any way.

EXAMPLE 1

Synthesis of N-(4-fluorophenyl)-N-(1-methylethyl)-2-|(5-trifluoromethyl)-1,3,4-thiadiazol-2-yl)oxy| acetamide-(Fluthiamide)

Dry FOE Hydroxy, dry TDA sulfone, recycled toluene were added to a reaction vessel. NaOH was slowly added over time to the vessel. The reaction mixture was then heated over time. The reaction conditions varied over ranges as shown in the Table below.

Toluene/FOE-hydroxy Mole Ratio 5.90–6.60
TDAS/FOE-hydroxy Mole Ratio 1.00–1.15
NaOH/FOE-hydroxy Mole Ratio 1.25–1.75
NaOH Concentration (wt. percent) 25–50
NaOH Add Time 1–3 hours
Reaction Temperature 5–15° C.
Reaction Time 1–3 hours

EXAMPLE 2

Recovery of Fluthiamide Using Acid

Fluthiamide, produced in accordance with Example 1, was recovered using acid. The reaction mixture from Example 1 was charged with process water and sulfuric acid (70%) to the desired pH. The temperature was adjusted and the mixture was filtered. The phases were then separated.

The above reaction and phase separation procedures resulted in an acidic organic mixture of fluthiamide in toluene. Isolation of fluthiamide was accomplished by two different methods. In a first method, toluene was removed by batch atmospheric steam distillation leaving a mixture of molten fluthiamide in water. Fluthiamide was isolated via solidification and filtration and drying. This method produced fluthiamide with an average A.I of about 92%.

In a second method, toluene was removed by batch atmospheric steam distillation leaving a mixture of molten fluthiamide in water. The bottom, heavy phase was separated. Fluthiamide was isolated from the heavy organic phase via flaking. This method produced fluthiamide with an average A.I. of about 88%.

EXAMPLE 3

Synthesis of N-(4-fluorophenyl)-N-(1-methylethyl)-2-|(5-trifluoromethyl)-1,3,4-thiadiazol-2-yl)oxy| Aacetamide (Fluthiamide)

In a second series of studies, fluthiamide was made by adding dry FOE Hydroxy, TDA sulfone in toluene, and recycled toluene to a reaction vessel. NaOH was slowly added over time and the resulting mixture heated for a period of time The reaction conditions are set forth below.
Toluene/FOE-hydroxy Mole Ratio 6.00
TDAS/FOE-hydroxy Mole Ratio 1.00–1.03
NaOH/FOE-hydroxy Mole Ratio 1.30–1.35
NaOH Concentration 50 wt. %
NaOH Add Time 3 hours
Reaction Temperature 10–15° C.
Reaction Time 0–1 hours Recovery of fluthiamide was accomplished as set forth below:

EXAMPLE 4

Recovery Using Sulfuric Acid

In accordance with the hot sulfuric acid process, soft water and 70% sulfuric acid were charged to the reaction mixture from Example 3, above. The phase separation conditions are summarized in the following table.
$H_2O$/FOE-hydroxy wt. ratio 1.10
Phase Separation pH 2.5
Phase Separation Temp 70° C.
Filtration yes
Mode continuous The fluthiamide in toluene was retained for fluthiamide isolation. The $H_2SO_4$ aqueous phase was neutralized and send to a waste water system.

EXAMPLE 5

Isolation of Fluthiamide Using Solidification

The organic phase from Example 4 were used for isolation of fluthiamide. Toluene was removed from the phases using a continuous atmospheric steam strip in a packed column. The toluene was recycled to the TDA sulfone and fluthiamide reactions. After removal of the toluene, fluthiamide was left as a molten fluthiamide/aqueous mixture (the bottom, heavy phase). The fluthiamide was obtained from the bottom heavy phase via solidification in a tray.

EXAMPLE 6

Preparation of Fluthiamide Using Acid Before Phase Separation

Embodiment 1

0.25 Moles of TDA-sulfone, 0.25 moles of FOE-hydroxy and 1.085 moles of toluene were mixed together and cooled to 5° C. 0.3 Moles of sodium hydroxide in the form of a 40 weight percent solution was added to the reaction mixture over a 1 hour period of time. The temperature of the reaction mixture was maintained between 5° C. and 10° C. for about 2 hours. The resulting reaction mixture was acidified to a pH of 5.0 with 10 weight percent HCl. The aqueous and organic layers were separated. The aqueous layer was extracted with toluene and the toluene extract added to the organic layer. The final product, fluthiamide, was isolated using flaking after removal of the toluene. Fluthiamide produced in accordance with this embodiment had a purity of 97.1% A.I. and a net yield of 99%.

Embodiment 2

About 17 moles of toluene, 3 moles of TDA-sulfone and 3 moles of FOE-hydroxy were mixed together and cooled to a temperature of 5° C. 450 ml of a 25 weight percent aqueous solution of sodium hydroxide was added to the mixture over a 1 hour period of time. About 270 ml of water and 85.8 grams of a 70 weight percent solution of $H_2SO_4$ was added to the reaction mixture to decrease the pH from a value of 13 to a value of 2.8. The reaction mixture was then heated to a temperature of 45° C. and held at that temperature for 15 minutes. The reaction mixture was stirred and heated to 65° C. for about 30 minutes. 50 mls of water was added to the mixture and the mixture heated to 85° C. After two hours, the reaction mixture was filtered and the aqueous and organic phases separated. Toluene was stripped off the organic layer and fluthiamide isolated using flaking. Fluthiamide prepared in accordance with this embodiment, had a purity of 99.3% A.I. and a net yield of 99.6%.

Embodiment 3

About 3 moles of toluene, 0.5 moles of TDA-sulfone and 0.5 moles of FOE-hydroxy were mixed together and cooled to a temperature to a 5° C. 96 grams of a 25 weight percent sodium hydroxide solution was added over a period of time of 1 hour while maintaining the temperature at 5° C. Following the addition of sodium hydroxide, the reaction mixture was heated for an additional 1.5 hours at 5° C. The reaction mixture was then titrated with 16.3 grams of concentrated HCl and quenched with 55 grams of water. Following the addition of acid and water, the reaction mixture was heated to a temperature of 45° C. for 1.5 hours. The temperature was then increased to 65° C. and maintained at this temperature for an additional 35 minutes. The temperature of the reaction mixture was then increased to 85° C. and maintained at this temperature for about 15 to 20 minutes. The reaction mixture was cooled, filtered, and the organic and aqueous layers were separated. Fluthiamide was isolated from the organic layer by distilling off the toluene and isolating fluthiamide using flaking. When prepared in accordance with this embodiment, fluthiamide had with a purity of 96.9% A.I. and a net yield of 97.7%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing N-(4-fluorophenyl)-N-(1-methylethyl)-2-[(5-trifluoromethyl)-1,3,4-thidiazol-2-yl)oxy]acetamide comprising the steps of:

a) reacting 2-(methylsulfonyl)-5-(trifluoromethyl)-1,3,4-thiadiazole with N-(4-fluorophenyl)-2-hydroxy-N-(1-methylethyl)acetamide in the presence of an aqueous alkali, and in the presence of an aprotic, aromatic solvent to form an aqueous phase and an organic phase;

(b) acidifying the mixture by adding a mineral acid;

(c) separating the phases; and (d) recovering the N-(4-fluorophenyl)-N-(1-methylethyl)-2-[(5-trifluoromethyl)-1,3,4-thidiazol-2-yl)oxy] acetamide from the organic phase.

2. The process of claim 1 wherein the solvent is toluene, xylene, cumene or mesitylene.

3. The process of claim 2 wherein the solvent is toluene.

4. The process of claim 1 wherein the aqueous alkali is an aqueous alkali metal carbonate or an aqueous alkali metal hydroxide.

5. The process of claim 4 wherein the alkali metal is sodium.

6. The process of claim 4 wherein the alkali metal hydroxide is sodium hydroxide.

7. The process of claim 1 wherein the aqueous phase has a pH of from about 8 to about 14.

8. The process of claim 7 wherein the aqueous phase has a pH of from about 12 to about 14.

9. The process of claim 8 wherein the aqueous phase has a pH of about 13.

10. The process of claim 1 wherein 2-(methylsulfonyl)-5-(trifluoromethyl)-1,3,4-thiadiazole in toluene is mixed with N-(4-fluorophenyl)-2-hydroxy-N-(1-methylethyl) acetamide in toluene and aqueous alkali is added at a temperature of from about 0° C. to about 30° C.

11. The process of claim 10 wherein the temperature is from about 5° C. to about 15° C.

12. The process of claim 11 wherein the temperature is from about 5° C. to about 10° C.

13. The process of claim 1 wherein the molar ratio of 2-(methylsulfonyl)-5-(trifluoromethyl)-1,3,4-thiadiazole to N-(4-fluorophenyl)-2-hydroxy-N-(1-methylethyl)acetamide is from about 1.5:1 to about 1:1.5.

14. The process of claim 1 wherein the molar ratio of solvent to 2-(methylsulfonyl)-5-(trifluoromethyl)-1,3,4-thiadiazole is from about 1:1 to about 5:1.

15. The process of claim 1 wherein the pH of the reaction mixture is adjusted to a pH of from about 1.0 to about 6.0.

16. The process of claim 15 wherein the pH is from about 2.0 to about 5.0.

17. The process of claim 1 wherein the mineral acid is hydrochloric acid or sulfuric acid.

18. The process of claim 1 wherein the reaction mixture is heated to a temperature of from about 10° C. to about 90° C. after acidification.

19. The process of claim 18 wherein the reaction mixture is heated to a temperature of from about 30° C. to about 60° C.

20. The process of claim 18 wherein the reaction mixture is filtered after heating.

21. The process of claim 1 wherein the N-(4-fluorophenyl)-N-(1-methylethyl)-2-[(5-trifluoromethyl)-1,3,4-thiadiazol-2-yl)oxy]acetamide is recovered by acidifying the organic phase by adding a mineral acid, removing the solvent from the organic phase to form a molten material and isolating the N-(4-fluorophenyl)-N-(1-methylethyl)-2-[(5-trifluoromethyl)-1,3,4-thiadiazol-2-yl)oxy]acetamide from the molten material.

22. A process for preparing N-(4-fluorophenyl)-N-(1-methylethyl)-2-[(5-trifluoromethyl)-1,3,4-thiadiazol-2-yl) oxy]acetamide comprising adding 2-(methylsulfonyl)-5-(trifluoromethyl)-1,3,4-thiadiazole in toluene and N-(4-fluorophenyl)-2-hydroxy-N-(1-methylethyl)acetamide in toluene to a reaction vessel to form a reaction mixture, cooling the reaction mixture to about 0° C.–5° C., adding an aqueous solution of sodium hydroxide to the reaction mixture and maintaining the reaction mixture at a temperature of from about 5° C. to about 15° C. for a period of time ranging from about 1 hour to about 3 hours to form an aqueous phase, and an organic phase having a pH of from about 8 to about 14, acidifying the mixture, heating the phases to a temperature of from about 10° C. to about 90° C., filtering the reaction mixture, separating the phases, and recovering the N-(4-fluorophenyl)-N-(1-methylethyl)-2-[(5-trifluoromethyl)-1,3,4-thiadiazol-2-yl)oxy]acetamide from the organic phase.

* * * * *